(12) United States Patent
Priebe et al.

(10) Patent No.: US 8,071,811 B2
(45) Date of Patent: Dec. 6, 2011

(54) CONTRAST AGENTS

(75) Inventors: Hanno Priebe, Oslo (NO); Duncan Wynn, Amersham (GB); Robert James Domett Nairne, St. Albans (GB)

(73) Assignee: GE Healthcare AS, Oslo (NO)

( * ) Notice: Subject to any disclaimer, the term of this patent is extended or adjusted under 35 U.S.C. 154(b) by 765 days.

(21) Appl. No.: 12/279,086

(22) PCT Filed: Feb. 14, 2007

(86) PCT No.: PCT/NO2007/000048
§ 371 (c)(1),
(2), (4) Date: Aug. 12, 2008

(87) PCT Pub. No.: WO2007/094680
PCT Pub. Date: Aug. 23, 2007

(65) Prior Publication Data
US 2009/0010853 A1 Jan. 8, 2009

(30) Foreign Application Priority Data

Feb. 14, 2006 (NO) .................................. 20060710

(51) Int. Cl.
*C07C 233/05* (2006.01)
*A61K 49/04* (2006.01)

(52) U.S. Cl. .................................... 564/153; 424/9.452
(58) Field of Classification Search .................. 564/153; 424/9.452
See application file for complete search history.

(56) References Cited

U.S. PATENT DOCUMENTS 5,817,873 A   10/1998   Meyer et al.

FOREIGN PATENT DOCUMENTS

| | | |
|---|---|---|
| DE | 936928 | 2/1956 |
| DE | 962698 | 4/1957 |
| EP | 0782563 | 6/1999 |
| WO | 95/01966 | 1/1995 |

OTHER PUBLICATIONS

PCT/NO2007/000048 Int'l Search Report/Written Opinion dated Jul. 2007.

*Primary Examiner* — Shailendra Kumar

(57) ABSTRACT

The present invention relates to a class of compounds and to diagnostic compositions containing such compounds where the compounds are iodine containing compounds. More specifically the iodine containing compounds are chemical compounds containing an aliphatic central moiety allowing for the arrangement of three iodinated phenyl groups bound thereto. The invention also relates to the use of such diagnostic compositions as contrast agents in diagnostic imaging and in particular in X-ray imaging and to contrast media containing such compounds.

20 Claims, No Drawings

CONTRAST AGENTS

This application is a filing under 35 U.S.C. 371 of international application number PCT/NO2007/000048, filed Feb. 14, 2007, which claims priority to application number 20060710 filed Feb. 14, 2006, in Norway the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing an aliphatic central moiety allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds in one or more of the following properties: renal toxicity, osmolality, viscosity, solubility, injection volumes/iodine concentration and attenuation/radiation dose.

SUMMARY OF THE INVENTION

The present invention provides compounds useful as contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central aliphatic moiety, allowing for the arrangement of three iodinated phenyl groups bound to thereto. The iodine containing contrast enhancing compounds can be synthesized from commercially available and relatively inexpensive starting materials.

DETAILED DESCRIPTION OF THE INVENTION

The contrast enhancing compounds are synthetic chemical compounds of formula (I)

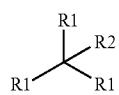

Formula (I)

wherein
   each $R^1$ denote the moiety —A—NB—R;
   $R^2$ denotes a hydrogen atom, a hydroxyl group, a $C_1$ to $C_4$ alkyl group or a $C_1$ to $C_4$ alkoxy group;
   each A are the same or different and are a $C_1$ to $C_4$ alkylene group optionally substituted by 1 to 3 hydroxyl groups;
   each B are the same or different and denotes a hydrogen atom and an acyl group;
   each R are the same or different and denote a triiodinated phenyl group, preferably a 2,4,6 triiodinated phenyl group, further substituted by two groups $R^3$ wherein each $R^3$ are the same or different and denote hydrogen or a non-ionic hydrophilic moiety,
   provided that at least one $R^3$ group in the compound of formula (I) is a hydrophilic moiety;
   and salts and optical isomers thereof.

In formula (I) each $R^2$ preferably denotes a hydrogen atom or a hydroxyl group.

Each group A preferably denotes a $C_1$ to $C_4$ alkylene group and more preferred denotes ethylene or methylene groups. Even more preferred all groups A are the same, and most preferred all A denote methylene groups.

Each B preferably denotes residues of aliphatic organic acids, and in particular a $C_1$ to $C_5$ organic acid such as formyl, acetyl, propionyl, butyryl, isobutyryl and valeriyl moieties. Hydroxylated and metoxylated acyl moieties are also feasible. In a further preferred embodiment all groups B are the same. In a particularly preferred embodiment all B groups in the compound of formula (I) are the same and denote the acetyl moiety.

The non-ionic hydrophilic moieties $R^3$ may be any of the non-ionizing groups conventionally used to enhance water solubility. Suitable groups include esters, amides and amine moieties that may be further substituted. Further substituents include straight chain or branched chain $C_{1-10}$ alkyl groups, preferably $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups.

In a preferred embodiment the hydrophilic moieties contain 1 to 6 hydroxy groups, preferably 1 to 3 hydroxy groups.
   The $R^3$ groups of the formulas listed below are preferred:
      —CONH—$CH_2$—$CH_2$—OH
      —CONH—$CH_2$—CHOH—$CH_2$—OH
      —CON($CH_3$)$CH_2$—CHOH—$CH_2$OH
      —CONH—CH—($CH_2$—OH)$_2$
      —CON—($CH_2$—$CH_2$—OH)$_2$
      —CONH$_2$
      —CONH$CH_3$
      —NHCO$CH_2$OH
      —N(CO$CH_3$)H
      —N(CO$CH_3$) $C_{1-3}$ alkyl
      —N(CO$CH_3$)—mono, bis or tris-hydroxy $C_{1-4}$ alkyl
      —N(CO$CH_2$OH)—hydrogen, mono, bis or tris-hydroxy $C_{1-4}$ alkyl
      —N(CO—CHOH—CH2OH)—hydrogen, mono, bis or trihydroxylated $C_{1-4}$alkyl.
      —N(CO—CHOH—CHOH—CH2OH)—hydrogen, mono, bis or trihydroxylated $C_{1-4}$ alkyl
      —N(CO$CH_2$OH)$_2$
      —CON($CH_2$—CHOH—$CH_2$—OH)($CH_2$—$CH_2$—OH)
      —CONH—C($CH_2$—OH)$_3$ and
      —CONH—CH($CH_2$—OH)(CHOH—$CH_2$—OH).
More preferably the $R^3$ groups will be equal or different and denote one or more moieties of the formulas —CON($CH_3$)$CH_2$—CHOH—$CH_2$OH, —CONH—$CH_2$—CHOH—$CH_2$—OH, —CONH—CH—($CH_2$—OH)$_2$, —CON—($CH_2$—$CH_2$—OH)$_2$, —CONH—$CH_2$—CHOH—$CH_2$—OH, —NHCO$CH_2$OH and —N(CO$CH_2$OH)—mono, bis or tris-hydroxy $C_{1-4}$ alkyl, and even more preferably all $R^3$ groups are equal and denote one of these moieties.

Even more preferred all $R^3$ are equal and denote a group of the formula —CONH—CH$_2$—CHOH—CH$_2$—OH.

Thus a preferred group of compounds of formula (I) according to the invention include the compounds of formula (II):

Formula (II)

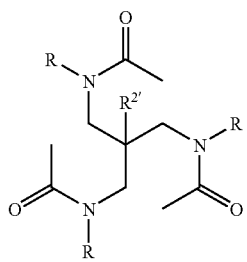

In formula (II) $R^{2'}$ denotes a hydrogen atom or a hydroxyl group and each group R are the same or different but are preferably the same and denote 2,4,6 triiodophenyl groups each substituted in the 3 and 5 position with non-ionic hydrophilic moieties $R^3$.

In a particularly preferred embodiment the compounds of formula (IIIa) to (IIId) are provided:

Formula (IIIa)

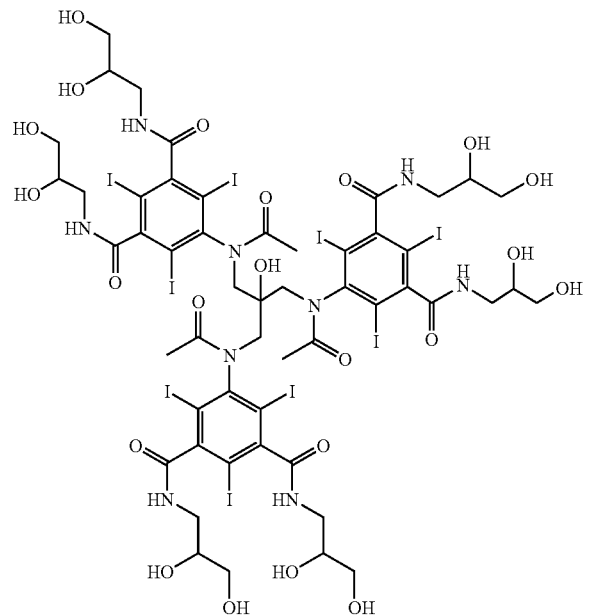

In formula (IIIa) all groups A of formula (I) denote a methylene moiety, all B groups denote acetyl groups, $R^2$ denote a hydroxyl group, and all groups R are the same and denote 2,4,6-triiodo-3,5-bis-(2,3-dihydroxy-propylcarbamoyl)-phenyl groups.

Formula (IIIb)

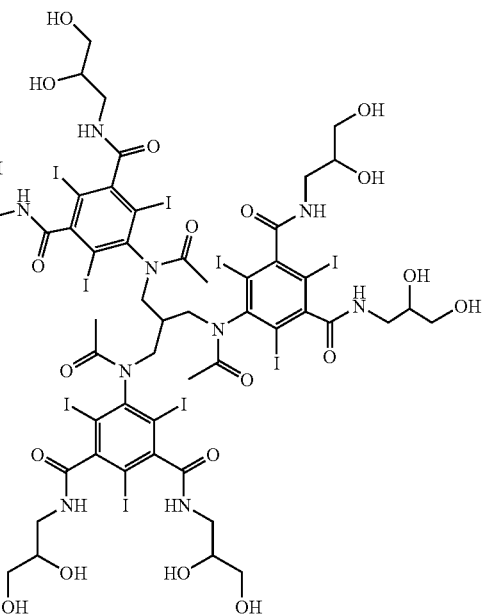

In formula (IIIb) all groups A of formula (I) denote a methylene moiety, all B groups denote acetyl groups, $R^2$ denote a hydrogen atom, and all groups R are the same and denote 2,4,6-triiodo-3,5-bis-(2,3-dihydroxy-propylcarbamoyl)-phenyl groups.

Formula (IIIc)

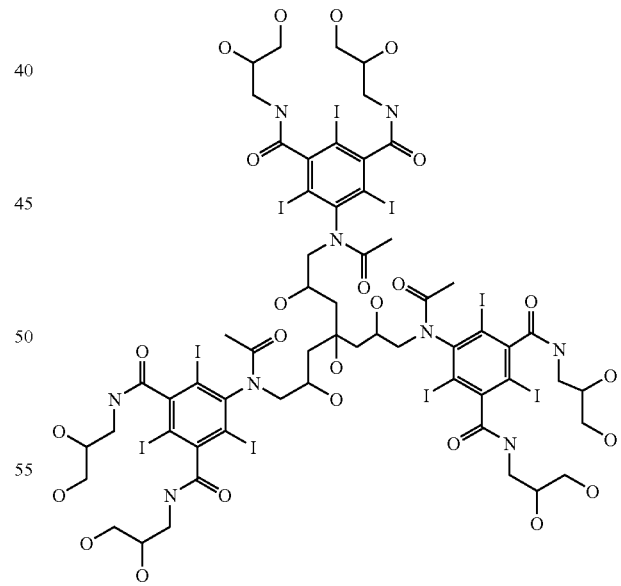

In formula (IIIc) all groups A of formula (I) denote a 2-hydroxypropylene moiety, all B groups denote acetyl groups, $R^2$ denote a hydroxyl group, and all groups R are the same and denote 2,4,6-triiodo-3,5-bis-(2,3-dihydroxy-propylcarbamoyl)-phenyl groups.

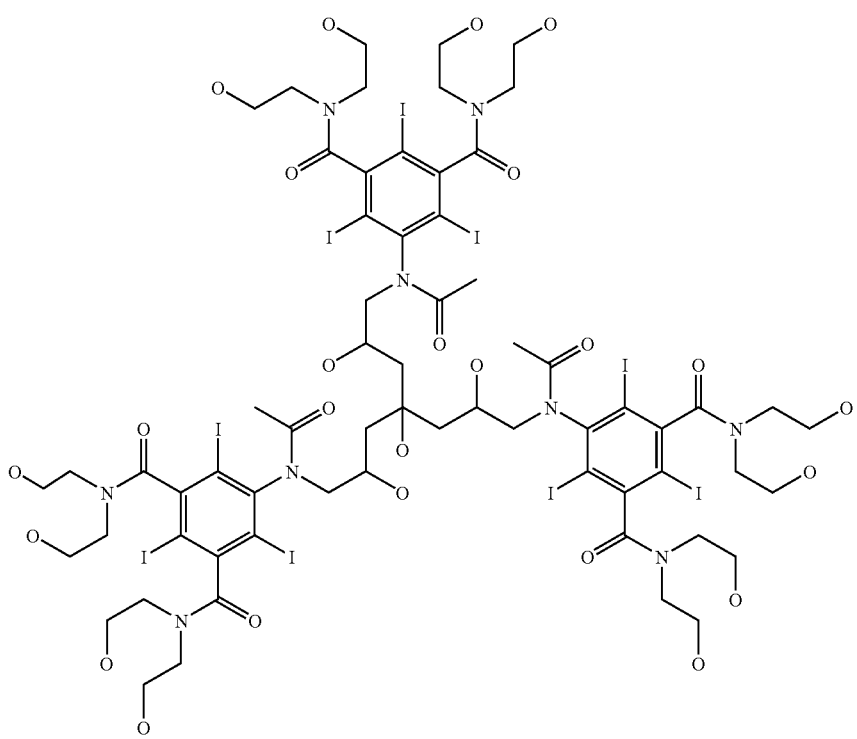

Formula (IIId)

In formula (IIId) all groups A of formula (I) denote a 2-hydroxypropylene moiety, all B groups denote acetyl groups, $R^2$ denote a hydroxyl group, and all groups R are the same and denote 2,4,6-triiodo-3,5-bis-(di(2-hydroxyetyl)-carbamoyl)-phenyl groups.

The compounds of formula (I) will attain a star-form with the relatively bulky iodinated phenyl substituents filling up the area between the 3 arms of the star. The molecule will therefore adopt a relatively round or globular form. Globular molecules will usually have enhanced solubility compared with similar molecules with a more planar structure.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

The compounds of the general formula (I) can be synthesized by several synthetic pathways known or obvious to the skilled artisan. In general, the compounds of formula (I) may be produced by dissolving the acylamino-triiodophenyl derivate in aqueous methanol in presence of alkali hydroxide, optionally pH adjustment with boric acid before addition of the alkylating agent. The reaction is stopped by neutralisation to pH<7 and product isolation.

The structure of the central building blocks is of formula (IV)

$$C\,R^{2\prime\prime}(A\text{-Hal})_3 \qquad (IV)$$

wherein $R^{2\prime\prime}$ denotes the $R^2$ group or a precursor thereof and A is as denoted above. Hal denotes a reactive halogen atom, preferably chlorine or iodine. Compounds of formula (IV) are commercially available or can be prepared from the corresponding alcohol following the procedure in *Synthesis;* 89 1987; p742-744.

The central building block 2,2'-Bis-chloromethyl-oxirane was prepared from commercial 3-Chloro-2-chloromethyl-propene, formic acid and $H_2O_2$ according to GB 1156708. It can be obvious be formed in situ from precursors like 2,3-Dichloro-2-chloromethyl-propan-1-ol or 1,3-Dichloro-2-chloromethyl-propan-2-ol in presence of base:

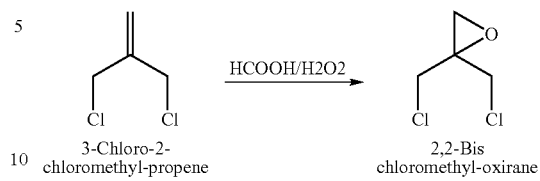

Tri-iodinated phenyl groups are commercially available or can be produced following procedures described or referred to e.g. in WO95/35122 and WO98/52911. The preferred tri-iodinated compound 5-amino-2,4,6-triiodo-N,N'-bis(2,3-dihydroxypropyl)-isophtalamide is commercially available e.g. from Fuji Chemical Industries, Ltd. The production of 5-N-acetylated compounds and corresponding acylated compounds can be effected by any conventional acylation agent such as acetylation with acetic acid anhydride, as described in U.S. Pat. No. 4,250,113.

The general procedure can be illustrated by the scheme below, where a compound of formula (IIIa) is produced. The acylamino-triiodophenyl derivate is dissolved in aqueous methanol in presence of alkali hydroxide. Optionally the start pH can be adjusted with boric acid before addition of the alkylating agent. The reaction is stopped by neutralisation to pH<7 and the product is isolated by preparative HPLC. A similar procedure is followed for the preparation of the compound of formula (IIIb), (IIIc) and (IIId), reacting the acylamino-triiodophenyl derivative with the appropriate halogenated compound of formula (IV).

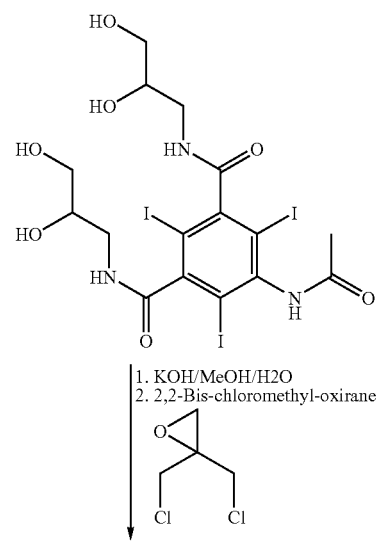

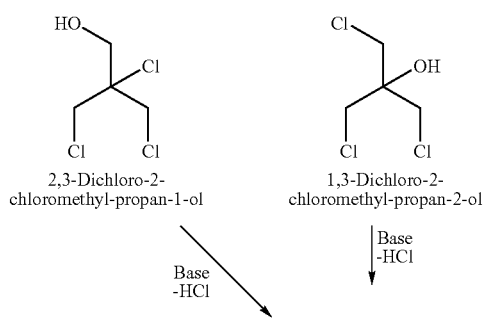

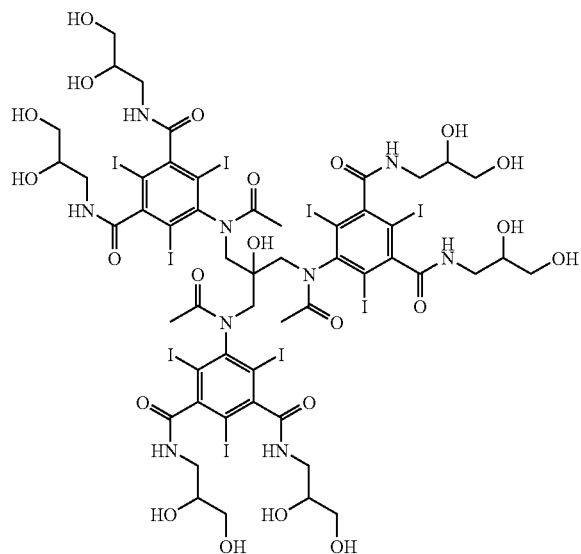

EXAMPLE 1

5-[Acetyl-(3-[acetyl-(2,4,6-triiodo-3,5-bis-(2,3-dihydroxy-propylcarbamoyl)-phenyl)-amino]-2-{[acetyl-(2,4,6-triiodo-3,5-bis-(2,3-dihydroxy-propylcarbamoyl)-phenyl)-amino]-methyl}-2-hydroxy-propyl)-amino]-N,N'-bis-(2,3-dihydroxy-propyl)-2,4,6-triiodo-isophthalamide

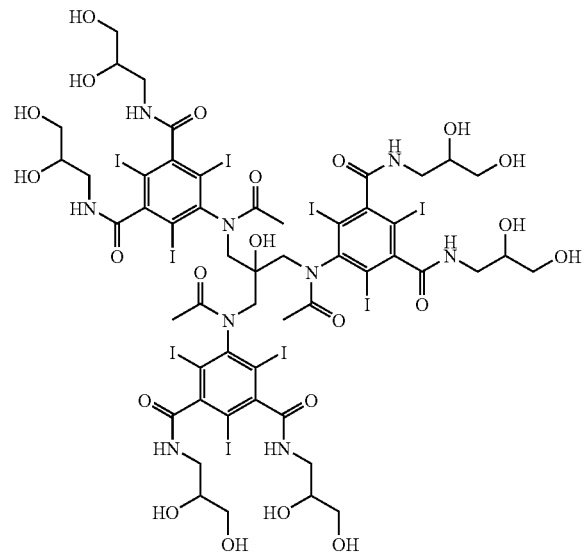

2-Chloromethyl-epichlorohydrin was prepared according to GB1156708. At 23-50° C. 5-Acetylamino-N,N'-bis-(2,3-dihydroxy-propyl)-2,4,6-triiodo-isophthalamide (552 g, 739 mmol) was dissolved in a solution of KOH (60.96 g, 994 mmol) in water (276 ml) and methanol (276 ml). To the clear solution boric acid (27.95 g, 443 mmol) is added and stirred for 0.5-3 h. At 23-25° C. 2-Chloromethyl-epichlorohydrin (12.86 g, 91.2 mmol) was added and stirred for 5 d. The reaction was stopped by adding water (1200 ml) and neutralization with 18.4% aqueous HCl to pH 4-5. A white precipitate (starting material) was filtered and the filtercake washed with water. Salts were removed from the filtrate by ion exchangers Amberlite 200C and IRA67. The solution contains 0.5-3 HPLC area % target compound (ca. 3 g) and the product was isolated by prep. HPLC.

HPLC/MS (TOF ES+, m/e): 2309.7 [M+H]+, 1155,3 [M+2H]$^{2+}$.

$^1$H NMR (d6-DMSO): NH:OH:CH$_3$=6:13:9

$^1$H NMR (D$_2$O): CH$_2$:CH$_3$=36:9

IR: 3277 (m), 2934 (w), 1647 (s), 1560 (m), 1430 (w), 1394 (m), 1271 (s), 1166 (w), 1111 (w), 1042 (m), 980 (w).

EXAMPLE 2

Preparation of tris(N-acetyl-N-(3,5-bis(2',3'-dihydroxypropylaminocarbonyl)-2,4,6-triiodophenyl) aminomethyl)methane (Formula IIIb)

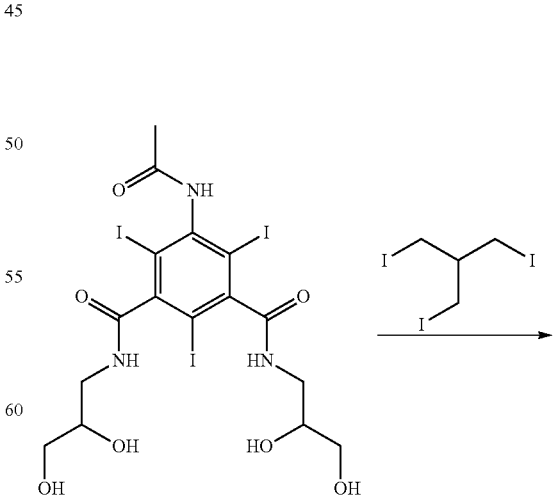

-continued

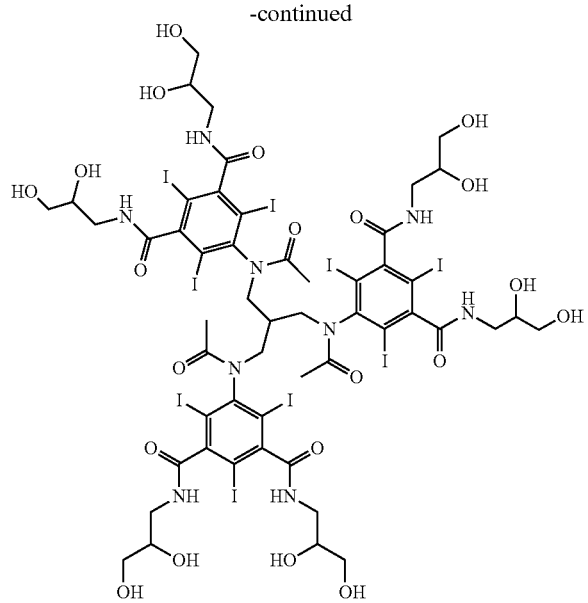

N-(3,5-bis(2',3'-dihydroxypropylaminocarbonyl)-2,4,6-triiodophenyl)acetamide (3.7 g, 5 mmol) is dissolved in methanol/water (6 ml) containing potassium hydroxide (400 mg, 7.2 mmol) at 40 C. Boric acid (0.44 g, 7.2 mmol) is added and the mixture cooled to 10 C. 2-Iodomethyl-1,3-diiodopropane (435 mg, 1 mmol, *Synthesis;* 89 1987; p742-744) is added and the mixture stirred at ambient temperature for 2 days. The reaction is quenched by adjusting the pH to 3.5. The unreacted starting material is filtered off and the filtrate is evaporated. The residue is purified by ion exchange and then HPLC.

EXAMPLE 3

Compound of Formula (IIIc)

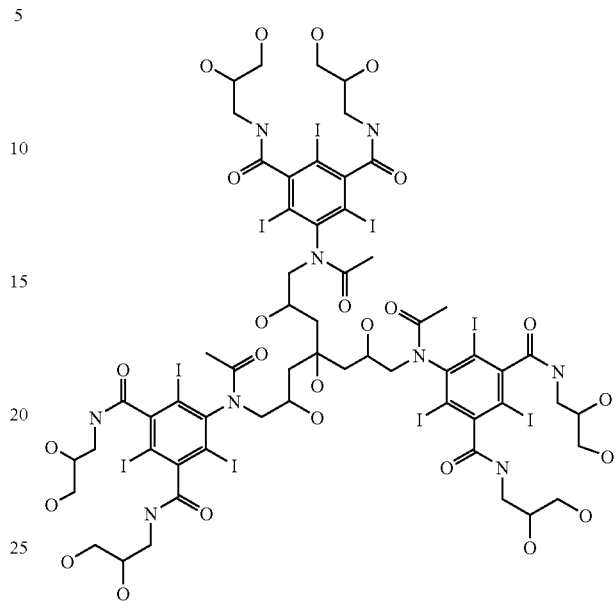

HPLC/MS (TOF ES+, m/e): 2441.8 [M+H]$^+$, 1221.4 [M+2H]$^{2+}$.

EXAMPLE 4

Compound of Formula (IIId)

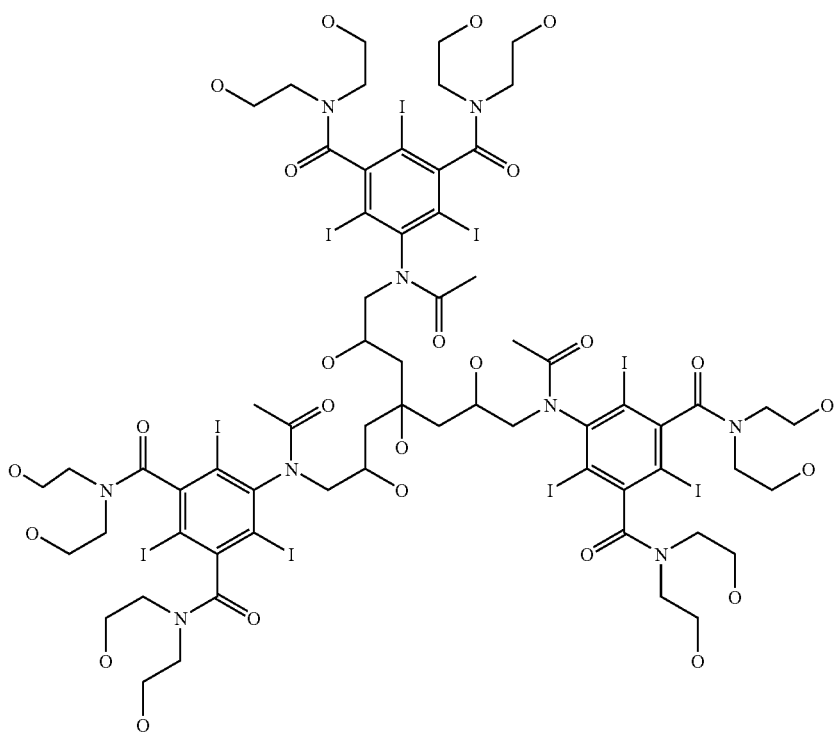

MS: (ESI Ion-Trap, m/e): 1263.4 [M+2H]$^+$

What is claimed is:

1. Compounds of formula (I)

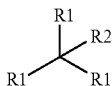

Formula (I)

wherein
each $R^1$ denote the moiety —A—NB—R;
$R^2$ denotes a hydrogen atom, a hydroxyl group, a $C_1$ to $C_4$ alkyl group or a $C_1$ to $C_4$ alkoxy group;
each A are the same or different and are a $C_1$ to $C_4$ alkylene group optionally substituted by 1 to 3 hydroxyl groups;
each B are the same or different and denotes a hydrogen atom and an acyl group;
each R are the same or different and denote a triiodinated phenyl group, further substituted by two groups $R^3$ wherein each $R^3$ are the same or different and denote hydrogen or a non-ionic hydrophilic moiety, provided that at least one $R^3$ group in the compound of formula one is a hydrophilic moiety; and salts and optical isomers thereof.

2. Compounds as claimed in claim 1 wherein $R^2$ denotes a hydrogen atom or a hydroxyl group.

3. Compounds as claimed in claim 1 wherein each A denotes a $C_1$ to $C_4$ alkylene group.

4. Compounds as claimed in claim 3 wherein each A denotes ethylene or methylene groups.

5. Compounds as claimed in claim 4 wherein all groups A are the same.

6. Compounds as claimed in claim 5 wherein each A denotes a methylene group.

7. Compounds as claimed in claim 1 wherein each B denotes a residue of aliphatic organic acids.

8. Compounds as claimed in claim 7 wherein each B denotes a $C_1$ to $C_5$ aliphatic organic acid residue such as formyl, acetyl, propionyl, butyryl, isobutyryl and valeriyl moieties.

9. Compounds as claimed in claim 8 wherein all groups B are the same.

10. Compounds as claimed in claim 9 wherein B denotes the acetyl moiety.

11. Compounds of claim 1 of formula (II)

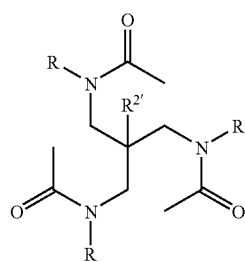

Formula (II)

wherein $R^{2'}$ denotes a hydrogen atom or a hydroxyl group and each group R denote 2,4,6 triiodophenyl groups each substituted in the 3 and 5 position with non-ionic hydrophilic moieties $R^3$.

12. Compounds as claimed in the preceding claims claim 1 wherein each $R^3$ denotes esters, amides and amine moieties that may be further substituted by straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

13. Compounds as claimed in claim 12 wherein each $R^3$ contain 1 to 6 hydroxy groups, preferably 1 to 3 hydroxy groups.

14. Compounds as claimed in claim 13 wherein each $R^3$ are the same or different and are polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups.

15. Compounds as claimed in claim 12 wherein each $R^3$ are the same or different and are selected from groups of the formulas
—CONH—$CH_2$—$CH_2$—OH
—CONH—$CH_2$—CHOH—$CH_2$—OH
—CON($CH_3$)$CH_2$—CHOH—$CH_2$OH
—CONH—CH—($CH_2$—OH)$_2$
—CON—($CH_2$—$CH_2$—OH)$_2$
—$CONH_2$
—$CONHCH_3$
—$NHCOCH_2$OH
—N($COCH_3$)H
—N($COCH_3$) $C_{1-3}$ alkyl
—N($COCH_3$)—mono, bis or tris-hydroxy $C_{1-4}$ alkyl
—N($COCH_2$OH)—hydrogen, mono, bis or tris-hydroxy $C_{1-4}$ alkyl
—N(CO—CHOH—CH2OH)—hydrogen, mono, bis or trihydroxylated $C_{1-4}$ alkyl.
—N(CO—CHOH—CHOH—CH2OH)—hydrogen, mono, bis or trihydroxylated $C_{1-4}$ alkyl
—N($COCH_2$OH)$_2$
—CON($CH_2$—CHOH—$CH_2$—OH)($CH_2$—$CH_2$—OH)
—CONH—C($CH_2$—OH)$_3$ and
—CONH—CH($CH_2$—OH)(CHOH—$CH_2$—OH).

16. Compounds as claimed in claim 15 wherein each $R^3$ are the same or different and are selected from groups of the formulas —CON($CH_3$)$CH_2$—CHOH—$CH_2$OH, —CONH—$CH_2$—CHOH—$CH_2$—OH, —CONH—CH—($CH_2$—OH)$_2$, —CON—($CH_2$—$CH_2$—OH)$_2$, —CONH—$CH_2$—CHOH—$CH_2$—OH, —$NHCOCH_2$OH and —N($COCH_2$OH)—mono, bis or tris-hydroxy $C_{1-4}$ alkyl.

17. Compounds as claimed in claim 1 wherein all groups $R^3$ are the same.

18. Compound as claimed in claim 17 being 5-[Acetyl-(3-[acetyl-(2,4,6-triiodo-3,5-bis-(2,3-dihydroxy-propylcarbamoyl)-phenyl)-amino]-2-{[acetyl-(2,4,6-triiodo-3,5-bis-(2,3-dihydroxy-propylcarbamoyl)-phenyl)-amino]-methyl}-2-hydroxy-propyl)-amino]-N,N'-bis-(2,3-dihydroxy-propyl)-2,4,6-triiodo-isophthalamide.

19. An X-ray diagnostic composition comprising a compound of formula (I) as defined in claim 1 together with pharmaceutically acceptable carriers or excipients.

20. A method of imaging, specifically X-ray imaging, comprising administration of compounds of formula (I) as defined in claim 1 to the human or animal body, examining the body with a diagnostic device and compiling data from the examination and optionally analysing the data.

* * * * *